United States Patent
Um Nlend (10) Patent No.: US 12,414,910 B2
(45) Date of Patent: Sep. 16, 2025

(54) SEMI-PERMANENT TATTOOS

(71) Applicant: inkbox ink incorporated, Toronto (CA)

(72) Inventor: Ingrid Um Nlend, Toronto (CA)

(73) Assignee: Inkbox Ink Incorporated, Toronto (CA)

( * ) Notice: Subject to any disclaimer, the term of this patent is extended or adjusted under 35 U.S.C. 154(b) by 468 days.

(21) Appl. No.: 17/822,261

(22) Filed: Aug. 25, 2022

(65) Prior Publication Data
US 2023/0073597 A1    Mar. 9, 2023

Related U.S. Application Data

(60) Provisional application No. 63/236,868, filed on Aug. 25, 2021.

(51) Int. Cl.
| | | |
|---|---|---|
| *A61K 8/892* | (2006.01) | |
| *A61K 8/34* | (2006.01) | |
| *A61K 8/35* | (2006.01) | |
| *A61K 8/44* | (2006.01) | |
| *A61K 8/49* | (2006.01) | |
| *A61K 8/81* | (2006.01) | |
| *A61K 8/895* | (2006.01) | |
| *A61Q 1/02* | (2006.01) | |

(52) U.S. Cl.
CPC .............. *A61K 8/892* (2013.01); *A61K 8/345* (2013.01); *A61K 8/347* (2013.01); *A61K 8/355* (2013.01); *A61K 8/44* (2013.01); *A61K 8/498* (2013.01); *A61K 8/8152* (2013.01); *A61K 8/895* (2013.01); *A61Q 1/025* (2013.01); *A61K 2800/524* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 6,022,551 A * | 2/2000 | Jampani | ................ | A61P 31/10 |
| | | | | 514/642 |
| 2005/0129742 A1 * | 6/2005 | Bringley | ................ | A61K 33/34 |
| | | | | 424/443 |
| 2008/0269694 A1 * | 10/2008 | Pieringer | ................ | A61B 90/39 |
| | | | | 604/218 |
| 2012/0128618 A1 * | 5/2012 | Claas | ................ | A61K 8/86 |
| | | | | 424/70.13 |
| 2017/0258956 A1 * | 9/2017 | Flach | ................ | A61L 15/44 |
| 2023/0210744 A1 * | 7/2023 | Um Nlend | ................ | A61K 8/8147 |
| | | | | 424/63 |
| 2024/0033200 A1 * | 2/2024 | Caputo | ................ | C07F 7/1804 |

FOREIGN PATENT DOCUMENTS

CN          110226975 A   *   9/2019

OTHER PUBLICATIONS

Stencil Stuff Gel SDS, Concentration Aloe Corp., Dec. 4, 2018 p. 1 (Year: 2018).*
Daveb, "Understanding the Stencil Process, Plus My Simple but Effective DIY Stencil Solution!", Tattooing 101, Mar. 29, 2013. Retrieved on Nov. 27, 2024 from https://tattooing101.com/forums/threads/understanding-the-stencil-process-plus-my-simple-but-effective-diy-stencil-solution.5701/ (Year: 2013).*
Naturally Balmy, "Preservative 12 SDS", pp. 1-2 Jan. 5, 2020 (Year: 2020).*
English translation of Chinese patent No. CN-110226975-A, published Sep. 13, 2019 (Year: 2019).*
Ahern, H. "Biochemical, Reagents Kits Offer Scientists Good Return on Investment", 1995, The Scientist, pp. 3-4 (Year: 1995).*
Aldous, H., "Basics of Tattooing for Beginners", Jun. 12, 2021, retrieved on Dec. 19, 2024. Retrieved from the internet: https://tattoo-spark.com/what-are-the-basics-of-tattooing-for-beginners/ (Year: 2021).*

* cited by examiner

*Primary Examiner* — Frederick F Krass
*Assistant Examiner* — Colman Welles
(74) *Attorney, Agent, or Firm* — Bookoff McAndrews, PLLC (57) ABSTRACT

Embodiments described herein include semi-permanent inks (e.g., semi-permanent inks contains genipin, a genipin derivative, lawsone, a lawsone derivative, or combinations thereof); semi-permanent ink applicators; transfer mediums; silicone adhesives; and silicone mediums and kits containing two or more thereof. Some embodiments describe methods for applying an ink to skin as well as methods for increasing the darkness of a semi-permanent tattoo and/or increasing the longevity of a semi-permanent tattoo.

13 Claims, 4 Drawing Sheets

SEMI-PERMANENT TATTOOS

CROSS REFERENCE TO RELATED APPLICATION

This application claims priority from U.S. Provisional Patent Application No. 63/236,868, filed on Aug. 25, 2021, the entire contents of which are incorporated herein by reference.

TECHNICAL FIELD

This invention relates to transfer mediums, silicone adhesives, and silicone mediums and methods for their use. This invention also relates to kits including two or more of a transfer medium; a silicone adhesive; a silicone medium; a semi-permanent ink; and an ink applicator, and methods for their use.

BACKGROUND

Temporary or semi-permanent tattoo or body inks have been used throughout human history to decorate the body. Generally, temporary or semi-permanent tattoos are both transferred to the skin through the direct exposure of the skin to tattoo ink over a designated incubation period. The quality of the transferred image and its duration on the skin can depend on the ink distribution profile in the outer layer of the skin called the stratum corneum. Current manufacturing processes for pre-fabricated tattoo designs include the utilization of flexographic or gravure printing, stencils, and inkjet printers. However, due to the barrier properties of the stratum corneum, many of the current methods require moderate oversight by the end user during the tattoo application process to ensure adequate ink delivery to the skin such that the tattoo ink develops properly. More specifically, in addition to the above, it can be of interest to provide a tattoo that has an increased darkness and/or an increased longevity on the skin of the user. Indeed, this makes it possible for the tattoo to be sufficiently apparent on the skin of the user, and/or for the tattoo to last on the skin of the used and prevent it from disappearing quickly.

SUMMARY

Provided herein are transfer mediums comprising: a solvent present in an amount of about 85% to about 95% w/w of the transfer medium; a thickening agent present in an amount of about 1% to about 5% w/w of the transfer medium; and a humectant present in an amount of about 1% to about 5% w/w of the transfer medium.

Also provided herein are method for applying ink to skin, the method comprising: (a) disposing a transfer medium on a portion of skin; (b) applying an applicator comprising ink disposed thereon to the portion of skin to thereby transfer the ink to the portion of skin; and (c) removing the applicator from the portion of skin. In some embodiments, the method further comprises: (d) depositing semi-permanent ink on the portion of the skin.

Also provided herein are methods for increasing the longevity of a semi-permanent ink in skin, the method comprising applying a silicone medium (e.g., any of the silicone mediums described herein) to the skin, more specifically upon application of the silicone medium over the semi-permanent ink.

Also provided herein are methods for increasing the darkness and/or longevity of a semi-permanent ink in skin, the method comprising applying a silicone adhesive (e.g., any of the silicone adhesives described herein) to the skin, more specifically upon application of the silicone adhesive over the semi-permanent ink.

Also provided herein are methods for increasing the speed at which the tattoo darkens, i.e. decreasing the time needed for achieving the final darkness of a semi-permanent ink in skin, the method comprising applying a silicone adhesive (e.g., any of the silicone adhesives described herein) to the skin, more specifically upon application of the silicone adhesive over the semi-permanent ink.

Also provided herein are kits comprising: a semi-permanent ink; a silicone adhesive and/or a silicone medium. In some embodiments, a kit described herein comprises: a transfer medium; and a silicone adhesive and/or a silicone medium. In some embodiments, a kit described herein comprises: a semi-permanent ink; a transfer medium; and a silicone adhesive and/or a silicone medium.

Also provided herein are silicone mediums comprising: dimethylpolysiloxane present in an amount of about 75% to about 85% w/w of the silicone medium; and hydroxy-terminated dimethyl siloxane present in an amount of about 5% to about 15% w/w of the silicone medium.

Reference to the term "about" has its usual meaning in the context of compositions to allow for reasonable variations in amounts that can achieve the same effect and also refers herein to a value of plus or minus 10% of the provided value. For example, "about 20" means or includes amounts from 18 to and including 22.

As used herein, a "colorant" refers to a substance that changes the color of reflected or transmitted light as the result of wavelength-selective absorption.

As used herein, a "temporary colorant" refers to a colorant (e.g., carbon black) that sits on top of the skin or, if it penetrates the skin, can diffuse out of the skin or can be washed off by, for example, water, soap, and/or isopropanol.

As used herein, "color" refers to wavelengths of electromagnetic radiation visible to the human eye.

A "surface" as described herein refers to a portion of a layer of material (e.g., backing, adhesive backing, an adhesive layer, etc.) that may be substantially parallel to a different layer. In some examples, the surface area of a surface of a particular layer described herein may be larger than the surface of an edge of the particular layer. For example, an edge of a particular layer can be substantially perpendicular to a surface of the particular layer. As used herein, the term "substantially" intends that the characteristic needs not be absolute, but is close enough so as to achieve the advantages of the characteristic. For example, "substantially parallel" is not limited to ab solute parallelism, and can include orientations that are intended to be parallel but due to manufacturing limitations may not be precisely parallel. For example, "substantially parallel" features are at least closer to a parallel orientation than a perpendicular orientation, and generally are formed within a few degrees of parallel. Similarly, "substantially perpendicular" is not limited to absolute perpendicularity, and can include orientations that are intended to be parallel but due to manufacturing limitations may not be precisely parallel. For example, "substantially perpendicular" features are at least closer to a perpendicular orientation than a parallel orientation, e.g., within a few degrees of perpendicular.

Unless otherwise required by context, singular terms shall include pluralities and plural terms shall include the singular. As used herein, the singular form "a", "an", and "the" include plural references unless indicated otherwise. For example, "an" excipient includes one or more excipients.

The details of one or more embodiments of the invention are set forth in the accompanying drawings and the description below. Other features, objects, and advantages of the invention will be apparent from the description and drawings, and from the claims. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Provided herein are transfer mediums; silicone adhesives; and silicone mediums. Also provided herein are kits comprising two or more of (e.g., two, three, four, or all five of): a semi-permanent ink (e.g., a semi-permanent ink comprising genipin, a genipin derivative, lawsone, a lawsone derivative, or combinations thereof); a semi-permanent ink applicator; a transfer medium; a silicone adhesive; and a silicone medium. Also provided herein are methods for applying an ink to skin. In some embodiments, provided herein are method for increasing the darkness of a semi-permanent tattoo and/or increasing the longevity of a semi-permanent tattoo and/or increasing the speed at which the tattoo darkens, i.e. decreasing the time needed for achieving the final darkness of the tattoo.

Provided herein are transfer mediums. Such compositions can be useful, for example, for improving the transfer of an ink to the skin, so as to make the transfer easier and/or sharper. Thus, the transfer medium can be applied on the skin prior to the application of a semi-permanent ink (i.e. semi-permanent tattoo). More particularly, after the application of the transfer medium on the skin of a user, an ink (such as water-based pen ink, that can in particular comprise at least one dye, for example such as a medical-grade ink) can be transferred on a portion of the skin (at the portion on which the transfer medium was previously applied) for example by using an applicator such as a paper or plastic (in particular such as transfer paper, for example the paper commercialized as "Tracing Paper" by Haddon Press Ltd), so as to transfer a design or a shape from the applicator to the skin to create a pattern, and then the semi-permanent ink can be deposited either on the pattern, or to fill in the said pattern with the semi-permanent ink. The transfer medium improves the transfer of the ink (the medical-grade ink) on the skin, the transfer being more dark and/or sharp, so as to facilitate the final design (tattoo) with the semi-permanent ink for the user, thus resulting in a more clear and sharp design on the skin. The improved transfer of the ink from the applicator to the skin of the user via the transfer medium, allows the realization of complex designs which would have been difficult to realize directly on the skin with the semi-permanent ink without a predefined pattern as template.

In some of any of the embodiments described herein, a transfer medium comprises a solvent; a thickening agent; and a humectant.

In some of any of the embodiments described herein, the solvent is present in an amount of about 70% to about 99% w/w of the transfer medium. For example, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99% w/w of the transfer medium. In some embodiments, the solvent is present in an amount of about 70%, about 75%, about 80%, about 85%, about 90%, about 91%, about 92%, about 93%, about 94%, about 95%, about 96%, about 97%, about 98%, or about 99% w/w of the transfer medium. In some embodiments, the solvent is present in an amount of about 93% w/w of the transfer medium.

Non-limiting examples of solvents include water, methanol, ethanol, isopropanol, and diethylene glycol monoethyl ether. In some embodiments, the solvent is a volatile solvent, e.g., the solvent can evaporate or vaporize at room temperature. Non-limiting examples of volatile solvents include water, methanol, ethanol, and isopropanol. In some embodiments, the solvent is selected to have a low toxicity profile when used as described herein. For example, the solvent can be selected such that the amount of the solvent in a transfer medium (e.g., a transfer medium described herein) is not a toxic amount for contact with a human skin surface. In some of any of the embodiments described herein, the solvent comprises water.

As used herein, a "thickening agent" refers to an agent that increases the viscosity of a liquid. In some embodiments, the thickening agent increases the viscosity of the liquid without substantially changing other properties of the liquid. Non-limiting examples of thickening agents include starches, gums (e.g., natural and synthetic gums), cellulosics, and arabinogalactan. Non-limiting examples of starches include aluminum starch octenylsuccinate. Non-limiting examples of gums include xanthan gum, *sclerotium* gum, tragacanth gum, pectin, gum karaya, gum arabic, agar, guar gum, carrageenan, locust bean gum, alginate, alginin, gelatin, tara gum, gum ghatti, gellan gum, konjac gum, *cassia* gum, spruce gum, chicle gum, dammar, curdlan gum, and pullulan. Non-limiting examples of cellulosics include hydroxyethylcellulose, hydroxypropyl cellulose, hydroxypropyl methylcellulose, ethylcellulose, soybean hemicellulose, and sodium carboxy methylcellulose.

In some of any of the embodiments described herein, the thickening agent is present in an amount of about 0.1% to about 10% w/w of the transfer medium. For example, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% w/w of the transfer medium. In some embodiments, the thickening agent is present in an amount of about 0.1%, about 1%, about 1.5%, about 2%, about 2.5%, about 3%, about 3.5%, about 4%, about 4.5%, about 5%, about 6%, about 7%, about 8%, about 9%, or about 10% w/w of the transfer medium. In some embodiments, the thickening agent is present in an amount of about 3.5% w/w of the transfer medium.

In some embodiments, the thickening agent comprises a crosslinked polyacrylate polymer, acrylates copolymer, or combinations thereof. In some embodiments, the crosslinked polyacrylate polymer is polyvinyl carboxy polymer crosslinked with ethers of pentaerythritol.

A "humectant" as used herein refers to a substance that attracts water. For example, a humectant may attract water to bring moisture to the skin. Non-limiting examples of humectants include polyhydric alcohols, for example, polyalkylene glycols (e.g., alkylene polyols and their derivatives), alpha hydroxy acids, sugars, Aloe vera gel, vegetable oil, lithium chloride, allantoin, urea, and dicyanamide. Non-limiting examples of polyhydric alcohols include glycerol, lactic acid, propylene glycol, propanediol, polyethylene glycol, dipropylene glycol, polypropylene glycol, polyethylene glycol and derivatives thereof, hexylene glycol, 1,3-butylene glycol, 1,2,6-hexanetriol, ethoxylated glycerol, propoxylated glycerol, glyceryl triacetate, sorbitol, hydroxypropyl sorbitol, xylitol, maltitol, hyaluronic acid, Tremella extract, sodium lactate, sodium L-pyroglutamate urea, and pyrrolidone carboxylic acid.

In some of any of the embodiments described herein, the humectant is present in an amount of about 0.1% to about 10% w/w of the transfer medium. For example, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% w/w of the transfer medium. In some embodiments, the humectant is present in an amount of about 0.1%, about 1%, about 1.5%, about 2%, about 2.5%, about 3%, about 3.5%, about 4%, about 4.5%, about 5%, about 6%, about 7%, about 8%, about 9%, or about 10% w/w of the transfer medium. In some embodiments, the humectant is present in an amount of about 2% w/w of the transfer medium.

In some embodiments, the humectant comprises propanediol.

In some embodiments of any of the above embodiments, a transfer medium described herein further comprises a preservative. "Preservative" as used herein refers to an agent that protects against decay, discoloration, and/or spoilage. Non-limiting examples of a preservative include ascorbic acid, an ascorbate, a palmitate, citric acid, a benzoate, a benzoic acid, a propionate, propionic acid, a sorbate, sorbic acid, a salicylic acid, a salicylate, hexa-2,4-dienoic acid, a hexa-2,4-dienoate, formaldehyde, a formaldehyde releaser, formic acid and its salts, 3-acetyl-6-methylpyran-2,4-(3H)-dione and its salts, 3,3'-dibromo-4,4'-hexamethylenedioxydibenzamidine and its salts, thiomersal, phenylmercuric salts, undec-10-enoic acid and its salts, 1,3-bis (2-ethylhexyl) hexahydro-5-methyl-5-pyrimidine, 5-bromo-5-nitro-1,3-dioxane, bronopol, 2,4-dichlorobenzyl alcohol, 1-(4-chlorophenyl)-3-(3,4-dichlorophenyl) urea, chlorocresol, chloroxylenol, 5-chloro-2-(2,4-dichlorophenoxy) phenol, N,N"-methylenebis[N'-[3-(hydroxymethyl)-2,5-dioxoimidazolidin-4-yl]urea], polyaminopropyl biguanide, methenamine, quaternium-15, climbazole, DMDM hydantoin, benzyl alcohol, 1-Hydroxy-4-methyl-6-(2,4,4-trimethylpentyl)-2-pyridon, piroctone olamine, bromochlorophene, o-cymen-5-ol, chlorophene, chloroacetaminde, methylchloroisothiazolinone, methylisothiazolinone, phenoxyisopropanol, chlorhexidine, chlorhexidine diacetate, chlorhexidine digluconate, chlorhexidine dihydrochloride, dimethyl oxazolidine, behentrimonium chloride, cetri-monium bromide, cetrimonium chloride, laurtrimonium bromide, laurtrimonium chloride, steartrimonium bromide, steartrimonium chloride, diazolidinyl urea, hexamidine, hexamidine diisethionate, hexamidine paraben, glutaral, 7-ethylbicyclooxazolidine, chlorphenesin, sodium hydroxymethylglycinate, silver chloride, benzethonium chloride, benzalkonium chloride, benzalkonium bromide, benzalkonium saccharinate, benzylhemiformal, iodopropynyl butylcarbamate, biphenyl-2-ol and its salts, pyrithionine zinc, an erythorbate, a nitrite, ethylenediaminetetraacetic acid (EDTA), sodium phytate (or phytic acid sodium salt hydrate), sodium lignosulfonate, butylated hydroxyanisole (BHA), butylated hydroxytoluene (BHT), capryllic acid, dilauryl thiodipropionate, erythorbic acid, gum guaiac, methylparaben, a sulfite, a bisulfite, a metabisulfite, propyl gallatepy, propylparaben, stannous chloride, sulfur dioxide, thiodipropionic acid, an isothiazoline, a paraben, phenoxyethanol, ethylhexylglycerin, a glycol, and a tocopherol. In some embodiments, the perseverative is present in an amount of about 0.1% to about 5% w/w of the transfer medium. For example, about 0.1% to about 4%, about 0.1% to about 3%, about 0.1% to about 2%, about 0.1% to about 1.5%, about 0.1% to about 1%, about 0.1% to about 0.5%, about 0.5% to about 4%, about 0.5% to about 3%, about 0.5% to about 2%, about 0.5% to about 1.5%, about 0.5% to about 1%, about 1% to about 5%, about 1% to about 4%, about 1% to about 3%, about 1% to about 2%, about 2% to about 5%, about 2% to about 4%, about 2% to about 3%, about 3% to about 5%, about 3% to about 4%, or about 4% to about 5% w/w of the transfer medium. In some embodiments, the perseverative is present in an amount of about 0.1%, about 0.5%, about 1%, about 1.5%, about 2%, about 2.5%, about 3%, about 3.5%, about 4%, about 4.5%, or about 5% w/w of the transfer medium. In some embodiments, the perseverative is present in an amount of 1% w/w of the transfer medium.

In some embodiments, the preservative comprises EDTA and/or sodium phytate. In some embodiments, the EDTA and/or sodium phytate is present in an amount of about 0.01% to about 1% w/w of the transfer medium. In some embodiments, the EDTA and/or sodium phytate is present in an amount of about 0.1% w/w of the transfer medium.

In some embodiments, the preservative is a combination of phenoxyethanol and ethylhexylglycerin (e.g., Euxyl® PE9010). In some embodiments, the combination of phenoxyethanol and ethylhexylglycerin is present in the composition at a ratio of about 9:1 phenoxyethanol:ethylhexylglycerin. In some embodiments, the combination of phenoxyethanol and ethylhexylglycerin is present in an amount of about 0.1% to about 2% w/w of the transfer medium. For example, about 0.1% to about 2%, about 0.1% to about 2%, about 0.1% to about 1.5%, about 0.1% to about 1%, about 0.1% to about 0.5%, about 0.5% to about 2%, about 0.5% to about 1.5%, about 0.5% to about 1%, about 1% to about 2%, about 1% to about 1.5%, or about 1.5% to about 2% w/w of the transfer medium. In some embodiments, the combination of phenoxyethanol and ethylhexylglycerin is present in an amount of about 1% w/w of the transfer medium.

In some embodiments of any of the above embodiments, a transfer medium described herein further comprises a pH adjuster. In some embodiments, the pH adjuster is present in an amount of about 0.1% to about 1% w/w of the transfer medium. For example, about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, about 0.1% to about 0.2%, about 0.2% to about 1%, about 0.2% to about 0.9%, about 0.2% to about 0.8%, about 0.2% to about 0.7%, about 0.2% to about 0.6%, about 0.2% to about 0.5%, about 0.2% to about 0.4%, about 0.2% to about 0.3%, about 0.3% to about 1%, about 0.3% to about 0.9%, about 0.3% to about 0.8%, about 0.3% to about 0.7%, about 0.3% to about 0.6%, about 0.3% to about 0.5%, about 0.3% to about 0.4%, about 0.4% to about 1%, about 0.4% to about 0.9%, about 0.4% to about 0.8%, about 0.4% to about 0.7%, about 0.4% to about 0.6%, about 0.4% to about 0.5%, about 0.5% to about 1%, about 0.5% to about 0.9%, about 0.5% to about 0.8%, about 0.5% to about 0.7%, about 0.5% to about 0.6%, about 0.6% to about 1%, about 0.6% to about 0.9%, about 0.6% to about 0.8%, about 0.6% to about 0.7%, about 0.7% to about 1%, about 0.7% to about 0.9%, about 0.7% to about 0.8%, about 0.8% to about 0.9%, about 0.8% to about 1%, or about 0.9% to about 1% w/w of the transfer medium. In some embodiments, the pH adjuster is present in an amount of about 0.1%, about 0.2%, about 0.3%, about 0.4%, about 0.5%, about 0.6%, about 0.7%, about 0.8%, about 0.9%, or about 1% w/w of the transfer medium.

In some embodiments, the pH adjuster comprises triethanolamine and/or sodium hydroxide.

In some embodiments, the composition is adjusted to a pH of about 4 to about 7. For example, about 4 to about 5, about 4.5 to about 5.5, about 5 to about 6, about 5.5 to about 6.5, or about 6 to about 7. In some embodiments, the composition is adjusted to a pH of about 4, about 4.25, about 4.5, about 4.75, about 5, about 5.25, about 5.5, about 5.75, about 6, about 6.25, about 6.5, about 6.75, or about 7. In some embodiments, the composition is adjusted to a pH of about 4 to about 6. In some embodiments, the composition is adjusted to a pH of about 4.6.

In some of any of the embodiments described herein, a transfer medium described herein can be formulated to be readily dispersed on skin. In some embodiments, the transfer medium is formulated to dry quickly upon application to skin. In some embodiments, the transfer medium is formulated to leave no residue upon drying on skin.

In some of any of the embodiments described herein, a transfer medium described herein can be formulated as a gel.

Also provided herein are silicone mediums. The silicone mediums can be applied on skin after the application of any semi-permanent ink (e.g., the semi-permanent inks described herein). Such compositions can be useful for, e.g., providing a protective barrier and/or increasing the longevity of a semi-permanent ink in skin. Silicone mediums can also be useful for one or more of: minimizing skin shedding; protecting skin; and moisturizing skin. In some embodiments, a silicone medium is a film barrier when applied to skin In some of any of the above embodiments, a silicone medium includes one or more silicones. As used herein, "silicone" refers to a polymer comprising siloxane. Non-limiting examples of a silicone include: dimethylpolysiloxane (also known as dimethicone, dodecamethylpentasiloxane, polydimethyl siloxane, or PDMS); decamethylcyclopentasiloxane; dodecamethyl cyclohexasiloxane; and hydroxy-terminated dimethyl siloxane.

In some of any of the above embodiments, a silicone medium includes one or more of (e.g., one, two, three, or all four of): dimethylpolysiloxane; decamethylcyclopentasiloxane; dodecamethyl cyclohexasiloxane; and hydroxy-terminated dimethyl siloxane. In some of any of the embodiments described herein, a silicone medium includes: dimethylpolysiloxane; decamethylcyclopentasiloxane; dodecamethyl cyclohexasiloxane; and hydroxy-terminated dimethyl siloxane. In some of any of the embodiments described herein, a silicone medium consists of one or more of (e.g., one, two, three, or all four of): dimethylpolysiloxane; dodecamethyl cyclohexasiloxane; decamethylcyclopentasiloxane; and hydroxy-terminated dimethyl siloxane.

In some of any of the above embodiments, a silicone medium includes dimethylpolysiloxane present in an amount of about 65% to about 90% w/w of the silicone medium. For example, about 65% to about 75%, about 70% to about 80%, about 75% to about 85%, or about 80% to about 90% w/w of the silicone medium.

In some of any of the above embodiments, a silicone medium includes hydroxy-terminated dimethyl siloxane present in an amount of about 5% to about 20% w/w of the silicone medium. For example, about 5% to about 10%, about 5% to about 15%, about 15% to about 20%, or about 10% to about 20% w/w of the silicone medium.

In some of any of the above embodiments, a silicone medium includes dodecamethyl cyclohexasiloxane present in an amount of less than about 1% of w/w of the silicone medium. In some embodiments, a silicone medium includes dodecamethyl cyclohexasiloxane present in an amount of less than about 0.001% to about 1% of w/w of the silicone medium.

In some of any of the above embodiments, a silicone medium includes decamethylcyclopentasiloxane present in an amount of less than about 1% of w/w of the silicone medium. In some embodiments, a silicone medium includes decamethylcyclopentasiloxane present in an amount of less than about 0.001% to about 1% of w/w of the silicone medium.

In some of any of the above embodiments, a silicone medium includes: dimethylpolysiloxane present in an amount of about 65% to about 90% w/w of the silicone medium; hydroxy-terminated dimethyl siloxane present in an amount of about 5% to about 20% w/w of the silicone medium; dodecamethyl cyclohexasiloxane present in an amount of less than about 0.001% to about 1% of w/w of the silicone medium; and decamethylcyclopentasiloxane present in an amount of less than about 0.001% to about 1% of w/w of the silicone medium.

In some of any of the above embodiments, a silicone medium includes: dimethylpolysiloxane present in an amount of about 75% to about 85% w/w of the silicone medium; hydroxy-terminated dimethyl siloxane present in an amount of about 5% to about 15% w/w of the silicone medium; dodecamethyl cyclohexasiloxane present in an amount of less than about 0.001% to about 1% of w/w of the silicone medium; and decamethylcyclopentasiloxane present in an amount of less than about 0.001% to about 1% of w/w of the silicone medium.

In some of any of the above embodiments, a silicone medium as described herein is formulated as a spray.

In some embodiments, a silicone medium as described herein does not include water. In some embodiments, a silicone medium as described herein includes less than about 0.1% water.

Also provided herein are kits including two or more of a semi-permanent ink; an ink applicator; a silicone adhesive; a silicone medium (e.g., any of the silicone mediums described herein); and a transfer medium (e.g., any of the silicone mediums described herein). In some embodiments, a kit includes a transfer medium (e.g., any of the transfer mediums described herein); and a silicone adhesive and/or a silicone medium (e.g., any of the silicone mediums described herein). In some embodiments, a kit includes a semi-permanent ink; an ink applicator; and a silicone adhesive and/or a silicone medium (e.g., any of the silicone mediums described herein). In some embodiments, a kit includes a semi-permanent ink; an ink applicator; a transfer medium (e.g., any of the transfer mediums described herein); and a silicone adhesive and/or a silicone medium (e.g., any of the silicone mediums described herein). In some embodiments, a kit includes a transfer medium (e.g., any of the transfer mediums described herein); and a silicone adhesive and/or a silicone medium (e.g., any of the silicone mediums described herein).

In some embodiments, the kit includes a silicone adhesive. A silicone adhesive can function as a protective barrier to prevent transfer onto other body parts while the active ingredients of the tattoo (semi-permanent ink) application process is working. Further, the application of a silicone adhesive can increase contact time between the ink and the skin of the user. A silicone adhesive can also act as an occlusive barrier that will increase the heat the application area. Heat can act as a catalyst to the reaction between the ink components (e.g., genipin) and amino acids. Silicone adhesives can be flexible and/or comfortable for the wearer.

In some embodiments, the silicone adhesive includes a silicone gel adhesive tape. In some embodiments, the silicone adhesive is coated on a surface. For example, in some embodiments, a silicone adhesive comprises a silicone adhesive disposed on a polycarbonate backing.

In some embodiments, the silicone adhesive has an adhesive coat weight of at least about 100 grams per square meter (gsm). For example, at least about 100 gsm, at least about 125 gsm, at least about 150 gsm, at least about 175 gsm, at least about 200 gsm, at least about 225 gsm, at least about 250 gsm, at least about 275 gsm, or at least about 300 gsm. In some embodiments, the silicone gel adhesive has an adhesive coat weight of about 100 gsm to about 300 gsm. For example, about 100 to about 125, about 100 to about 150, about 100 to about 175, about 100 to about 200, about 100 to about 225, about 100 to about 250, about 100 to about 275, about 100 to about 300, about 125 to about 150, about 125 to about 175, about 125 to about 200, about 125 to about 225, about 125 to about 250, about 125 to about 275, about 125 to about 300, about 150 to about 175, about 150 to about 200, about 150 to about 225, about 150 to about 250, about 150 to about 275, about 150 to about 300, about 175 to about 200, about 175 to about 225, about 175 to about 250, about 175 to about 275, about 175 to about 300, about 200 to about 225, about 200 to about 250, about 200 to about 275, about 200 to about 300, about 225 to about 250, about 225 to about 275, about 225 to about 300, about 250 to about 275, about 250 to about 300, or about 275 to about 300 gsm. In some embodiments, the silicone gel adhesive has an adhesive coat weight of about 100, about 125, about 150, about 175, about 200, about 225, about 250, about 275, or about 300 gsm.

In some of any of the above embodiments, the silicone adhesive is a silicone adhesive wrap. The silicone adhesive of the wrap can prevent interactions between the ink and the adhesive that will minimize optimal ink transfer onto the targeted area of application. Non-limiting examples of the silicone adhesive wraps include silicone gel adhesive tape with a clear polycarbonate backing and silicone gel adhesive tape lined onto a cohesive bandage.

In some of any of the above embodiments, the silicone adhesive can be removed from skin without causing trauma to the skin.

In some of any of the above embodiments, the silicone adhesive can be removed from skin and repositioned. In some embodiments, the silicone adhesive can be removed and later reapplied (e.g., reapplied a few hours later, one day later, or two days later).

In some of any of the above embodiments, the silicone adhesive can have a thickness of about 0.1 to about 0.5 mm. For example about 0.1 to about 0.2, about 0.1 to about 0.25, about 0.1 to about 0.3, about 0.1 to about 0.35, about 0.1 to about 0.4, about 0.1 to about 0.45, about 0.2 to about 0.25, about 0.2 to about 0.3, about 0.2 to about 0.35, about 0.2 to about 0.4, about 0.2 to about 0.45, about 0.2 to about 0.5, about 0.25 to about 0.3, about 0.25 to about 0.35, about 0.25 to about 0.4, about 0.25 to about 0.45, about 0.25 to about 0.5, about 0.3 to about 0.35, about 0.3 to about 0.4, about 0.3 to about 0.45, about 0.3 to about 0.5, about 0.35 to about 0.4, about 0.35 to about 0.45, about 0.35 to about 0.5, about 0.4 to about 0.45, about 0.4 to about 0.5, or about 0.45 to about 0.5 mm. In some of embodiments, the silicone adhesive can have a thickness of about 0.25 mm.

In some embodiments, a kit described herein includes a semi-permanent ink and/or an ink applicator. Non-limiting examples of semi-permanent inks and ink applicators that can be included in the kits described herein include those described in U.S. Publication No. 2020/0276101; International Application No. PCT/US2021/045767; U.S. Pat. No. 10,143,641, and U.S. Patent Application No. 63/037,381 each of which are hereby incorporated by reference in their entirety.

In some embodiments, a semi-permanent ink includes a semi-permanent colorant (e.g., genipin derivative, lawsone, lawsone derivative, or combinations thereof); a solvent; and a semi-volatile semi-permanent colorant solubilizer. U.S. Publication No. 2020/0276101 and International Application No. PCT/US2021/045767 describes, e.g., semi-permanent inks comprising, e.g., genipin, a genipin derivative, lawsone, a lawsone derivative, or combinations thereof, that can be suitable for inkjet printing. U.S. Publication No. 2020/0276101 and International Application No. PCT/US2021/045767 also describe ink applicators that can be used to apply a semi-permanent ink to skin.

In some embodiments, a semi-permanent ink includes a semi-permanent colorant (e.g., a genipin derivative, lawsone, a lawsone derivative, or a combination thereof) and one or more of: a solvent; a humectant; a thickening agent; and a film-forming agent. International Application No. PCT/US2021/045767 describes compositions suitable for use in a marker applicator and is incorporated herein by reference in its entirety.

In some of any of the above embodiments, a kit as described herein can further include an applicator. In some embodiments, the applicator comprises paper or plastic. Non-limiting examples of paper include parchment paper, tracing paper, stencil paper, and tattoo transfer paper. Examples, of tattoo transfer paper can include hectograph paper and thermal paper.

In some embodiments, the applicator is pre-cut. In some embodiments, the applicator is pre-cut into a rectangular shape.

In some of any of the above embodiments, a kit as described herein can further include ink. In some embodiments, the ink comprises medical-grade ink. In some embodiments, the ink is removable from skin using an alcohol.

In some embodiments, a kit as described herein can further include a skin priming composition. See, e.g., the skin priming compositions provided in U.S. Publication No. 2020/0276101. In some embodiments of the kit, a priming article, e.g., a towelette, may be provided with the skin priming composition. In some embodiments, the skin priming composition may be provided in the kit on a priming article, e.g., a towelette, premoistened with the skin priming composition.

In some embodiments, the kit further includes an aftercare composition. For example, the kit can further include an aftercare composition as described in U.S. Publication No. 2020/0276101.

In some of any of the above embodiments, a kit as described herein can further include a glove.

In some embodiments, a kit as described herein can further include instructions describing any of the methods described herein.

Additional ink (temporary and/or semi-permanent colorant) may be added to the kits described herein to allow e.g., correction, personalization, recoloring, etc. of the semi-permanent tattoo by freehand application. In some embodiments, the extra ink can have any of the compositions described in U.S. Publication No. 2020/0276101, U.S. Pat. No. 10,143,641, and International Application No. PCT/US2021/045767.

Also provided herein are methods for applying ink (first ink) to skin such as a water-based pen ink that can more specifically comprise at least a dye (in particular the ink is a cosmetically acceptable ink), the method comprising: disposing a transfer medium on a portion of skin; applying an applicator (such as plastic or paper) comprising ink (first ink) disposed thereon to the portion of skin to thereby transfer the ink (or part of the ink) to the portion of skin; and removing the applicator from the portion of skin.

In some embodiments, disposing a transfer medium on a portion of the skin comprises spreading the transfer medium on the portion of skin. In some embodiments, the transfer medium is spread on the portion of skin evenly. In some embodiments, the transfer medium is disposed on the portion of skin until the skin is damp. Therefore, upon the transfer of the ink (or part of the ink) to the portion of the skin (after the application of the transfer medium), a template is formed on the skin that will be used for the application of a further ink (second ink), such as a semi-permanent ink (second ink). Spreading the transfer medium on the portion of the skin prior to the application of the applicator with the ink disposed thereon, enhances the quality of the transfer of the ink (first ink), for example the transfer being darker and/or sharper).

In some embodiments, applying an applicator comprising ink (first ink) disposed thereon to the portion of skin to thereby transfer the ink to the portion of skin comprises maintaining contact between the applicator and the portion of the skin for about 1 to about 20 seconds (e.g., about 1 to about 5, about 1 to about 10, about 1 to about 15, about 5 to about 10, about 5 to about 15, about 5 to about 20, about 10 to about 15, about 10 to about 20, or about 5 to about 20 seconds).

In some of any of the above embodiments, the method further comprises: depositing semi-permanent ink (second ink) on the portion of the skin (e.g., any of the semi-permanent inks described herein). More specifically, the semi-permanent ink can be easily deposited on the portion of the skin, for example by following the pattern previously obtained thanks to the transfer of the ink upon the application of the applicator having the ink deposited thereon. In some embodiments, depositing semi-permanent ink on the portion of the skin comprises tracing the ink on the skin using a semi-permanent ink. In some embodiments, depositing semi-permanent ink on the portion of the skin comprises tracing the ink on the skin using a semi-permanent ink and ink applicator. In some embodiments, depositing semi-permanent ink on the portion of the skin comprises using two or more semi-permanent inks. In some embodiments, each semi-permanent ink is a different color than each other semi-permanent ink. In some embodiments, depositing semi-permanent ink on the portion of the skin comprises tracing the ink on the skin using two or more semi-permanent tattoo markers.

Also provided herein are methods for applying ink to skin, the method comprising: depositing ink (first ink) on a portion of skin and depositing semi-permanent ink (second ink) on the portion of the skin.

In some embodiments, a portion of the ink on the skin is traced. In some embodiments, the whole ink on the skin is traced.

In some embodiments, depositing semi-permanent ink on the portion of the skin comprises using the semi-permanent ink to fill in one or more portions of the ink on the skin. For example, if the ink on the skin forms one or more shapes, one or more of those shapes can be filled in using a semi-permanent ink. In some embodiments, depositing semi-permanent ink on the portion of the skin comprises using two or more semi-permanent inks to fill in one or more portions of the ink on the skin. In some embodiments, a first portion of the ink on the skin is filled in using a semi-permanent tattoo marker comprising a first color of a semi-permanent tattoo ink and a second portion of the ink on the skin is filled in using a semi-permanent tattoo marker comprising a second color of a semi-permanent tattoo ink.

In some of the above embodiments, the ink is disposed upon the paper using an ink. In some above embodiments, the ink is a medical-grade ink. In some embodiments, the ink is removable from skin using an alcohol. In some above embodiments, the alcohol comprises ethanol, isopropyl alcohol, or a combination thereof.

In some of any of the above embodiments, the ink is disposed on the applicator as a design, and wherein the design is a pattern, a shape, a symbol, one or more words, a picture, an image created by a user, or combinations thereof.

In some of any of the above embodiments, the ink is applied to the skin on a user's forearm, leg, shoulder, bicep, torso, face, neck, or back. In some embodiments, the semi-permanent ink is applied to the skin on a user's forearm, leg, shoulder, bicep, torso, face, neck, or back.

In some of any of the above embodiments, the method further comprises: (e) applying a silicone adhesive and/or a silicone medium to the skin over the semi-permanent tattoo (e.g., any of the silicone adhesives and/or silicone mediums described herein).

Also provided herein is the use of a transfer medium as described above, for increasing the transfer of an ink (such as a water-based pen ink, more specifically comprising at least a dye) from an applicator (such as paper or plastic) to the skin, when the applicator comprising the water-based pen ink is applied on the skin, after the application of the transfer medium on the skin.

Also provided herein are methods for increasing the longevity of a semi-permanent ink in skin, the method comprising applying a silicone medium (e.g., any of the silicone mediums described herein) to the skin.

In particular, also provided herein is the use of a silicone medium as described above for increasing the longevity of a semi-permanent ink in skin, upon application of the silicone medium to the skin.

In some of any of the above embodiments, the silicone medium is applied to the skin of a subject having a semi-permanent ink tattoo.

In some of any of the above embodiments, the silicone medium is applied to the skin over semi-permanent ink. For example, the silicone medium is applied to the skin over a portion of the semi-permanent ink or over the entire semi-permanent ink.

In some of any of the above embodiments, the silicone medium is applied to the skin periodically. For example, the silicone medium can be applied to the skin daily, twice daily, or every other day.

In some of any of the above embodiments, the method further comprises applying a silicone adhesive to the skin. In some above embodiments, the silicone adhesive is applied to the skin within about 0.5 to about 5 hours after the application of the semi-permanent ink to the skin. For example, about 0.5 to about 1, about 0.5 to about 2.5, about 1 to about 2.5, about 1 to about 5, or about 2.5 to about 5 hours after the application of the semi-permanent ink to the skin.

In some of any of the above embodiments, the silicone medium increases the longevity of the semi-permanent tattoo in the skin by about 1 to about 5 days. For example, by about 1 to about 2 days, about 1 to about 3 days, about 1 to about 4 days, or about 2 to about 3 days, about 2 to about 4 days, about 2 to about 5 days, about 3 to about 4 days, about 3 to about 5 days, or about 4 to about 5 days. In some of embodiments, the silicone medium increases the longevity of the semi-permanent tattoo in the skin by about 1, about 2, about 3, about 4, or about 5 days.

Also provided herein are methods for increasing the darkness of a semi-permanent ink in skin, the method comprising applying a silicone adhesive (e.g., any of the silicone adhesive described herein) to skin.

Also provided herein are methods for increasing the speed at which the tattoo darkens, i.e. decreasing the time needed for achieving the final (maximum) darkness of a semi-permanent ink in skin, the method comprising applying a silicone adhesive (e.g., any of the silicone adhesives described herein) to skin.

Also provided herein is the use of a silicone adhesive as described above for increasing the darkness of a semi-permanent ink in skin and/or for decreasing the time needed for achieving the final darkness of the semi-permanent tattoo, upon application of the silicone adhesive to the skin.

In some of any of the above embodiments, the silicone adhesive is applied to the skin over the semi-permanent tattoo. In some embodiments, the silicone adhesive is applied to the skin over a portion of the semi-permanent tattoo. In some of any of the above embodiments, the silicone adhesive is applied to the skin over the entire semi-permanent tattoo.

In some of any of the above embodiments, the silicone adhesive is applied to the skin within about 0.5 to about 5 hours after the application of the semi-permanent ink to the skin. For example, about 0.5 to about 1, about 0.5 to about 2.5, about 1 to about 2.5, about 1 to about 5, or about 2.5 to about 5 hours after the application of the semi-permanent ink to the skin.

In some of any of the above embodiments, the silicone adhesive is applied to the skin within about 1 hour after the application of the semi-permanent tattoo to the skin. In some embodiments, the silicone adhesive is applied to the skin about 10 minutes after the application of the semi-permanent tattoo to the skin. In some above embodiments, the silicone adhesive is applied to the skin about 5 minutes after the application of the semi-permanent tattoo to the skin.

In some of any of the above embodiments, the silicone adhesive is removed from the skin about 1 to about 10 hours after the application of the silicone adhesive to the skin. For example, the silicone adhesive is removed from the skin about 1 to about 2, about 1 to about 5, about 1 to about 7, about 2 to about 7, about 6 to about 8, or about 5 to about 10 hours after the application of the silicone adhesive to the skin.

In some of any of the above embodiments, the method further comprises applying a silicone medium (e.g., any of the silicone mediums described herein) to the skin.

In some of any of the above embodiments, the silicone medium is applied to the skin periodically. For example, the silicone medium can be applied to the skin daily, twice daily, or every other day.

The invention will be further described in the following examples, which do not limit the scope of the invention described in the claims.

EXAMPLES

Example 1. Preparation of a Transfer Gel

A transfer gel was prepared as show in Table 1.

TABLE 1

| Phase | Ingredient | % w/w |
|---|---|---|
| A | Water | 93 |
|  | Crosslinked polyacrylate polymer (e.g., CARBOMER ® 980) | 0.6 |
| B | Acrylates copolymer (e.g., CARBOPOL ® Aqua SF1) | 3 |

TABLE 1-continued

| Phase | Ingredient | % w/w |
|---|---|---|
| C | Propanediol (e.g., Zemea ®) | 2 |
| D | Disodium EDTA (e.g., EDTA BD) | 0.1 |
| E | Phenoxyethanol and Ethylhexylglycerin (e.g., EUXYL ® 9010 PE) | 1 |
| F | Triethanolamine (e.g., TEA 85) | 0.3 |

A design has been drawn on a transfer paper commercialized as "Tracing Paper" by Haddon Press Ltd with an aqueous-based pen ink comprising 75.90% of water, −20.70% of Glycerine and 3.40% of FD&C Red 40.

After application of the transfer gel composition on a portion of the skin of the user, wherein the transfer gel composition is spread evenly over the desired location of tattoo application, the transfer paper on which the design was drawn with aqueous-based pen ink is placed against the skin where the transfer gel composition was applied and held firmly for 5 to 10 seconds. The transfer paper is then removed and the transferred design allowed to set for an additional 5-10 seconds. The residual transfer gel composition is then wiped away from the skin. A semi-permanent tattoo ink can then be applied on the skin by the user, in particular by tracing over the transferred design, such as the semi-permanent ink (Tattoo Marker) composition comprising Genipa plant extract disclosed in U.S. 63/037,381 patent application.

It has been observed that the design that had been drawn on the transfer paper has indeed been efficiently transferred to the skin, i.e. the transferred image is of good quality (i.e. sufficiently sharp and dark) and creates a pattern that eases the application of a semi-permanent tattoo ink by the user in that it provides a pattern (i.e. a guide) for the application of the semi-permanent ink.

Example 2. Preparation of a Silicone Medium

A silicone medium was prepared as show in Table 2.

TABLE 2

| Ingredient | % w/w |
|---|---|
| Dimethicone (and) Dimethiconol (e.g., XIAMETER ® PMX-1503 Fluid Nexeo) | 64.7 |
| Dimethicone | 29.4 |
| Dimethicone and Dimethicone/Vinyl Dimethicone Crosspolymer (e.g., XIAMETER ® PMX-200 Silicone Fluid 2.0 cSt) | 5.9 |

Example 3. Use of a Silicone Adhesive

To compare the development time and maximum darkness of a tattoo achieved with semi-permanent ink on the skin, with and without a silicone adhesive, 4 half-filled circles were designed using a stencil and using a Tattoo Marker.

The silicone adhesive used is P-DERM®PS-2056 from Polymer Science. Said adhesive is a silicone gel adhesive tape consisting of a silicone gel adhesive which is coated onto a polyurethane carrier and is disposed on a polycarbonate backing layer. The silicone adhesive acts as a protective barrier to prevent transfer (and/or diffusion) onto other body parts while the active ingredients of the tattoo (semi-permanent ink) are working. In addition, the application of the silicone adhesive increases contact time between the semi-permanent ink and the skin of the user, and also acts as an occlusive barrier that increases the heat of the application area (as heat can act as a catalyst to the reaction between the semi-permanent ink components (e.g., genipin) and amino acids).

The semi-permanent ink (Tattoo Marker) composition that is used comprises Genipa plant extract and is close to the one disclosed in the U.S. 63/037,381 patent application to which was added Carbon Black. Such composition is detailed in the table 3 below:

TABLE 3

| | Ingredient | Amount (% w/w) | Amount (g) |
|---|---|---|---|
| Phase A | Aqua | 31.4 | 15.7 |
| | Glycerol | 4.0 | 2.0 |
| | Hydroxyethylcellulose | 0.05 | 0.025 |
| | Xanthan Gum | 0.05 | 0.025 |
| Phase B | Ethanol | 41.2 | 22.6 |
| | Genipa Plant Extract | 14.0 | 7.0 |
| | Polymethylsilsesquioxane | 2.0 | 1.0 |
| Additions | Acrylates/C12-22 Alkyl Methacrylate Copolymer | 3.0 | 1.5 |
| | Phenoxyethanol and) Ethylhexylglycerin | 1.0 | 0.5 |
| | 1,2-Hexanediol | 2.0 | 1 |
| | Carbon Black | 1.0 | 0.5 |
| | Sodium lignosulfonate | 0.3 | 0.15 |

5 minutes after application of the semi-permanent ink on the skin of a user, 2 designs (row S) were covered with the Silicone Adhesive, for 1 hour. 2 designs (row B) were left uncovered. The skin on which the tattoo has been applied is washed with water after 6 hours in order to remove the color deriving from carbon black (so that the darkness assessment of the tattoo on the skin can be made based solely on the color deriving from the semi-permanent ink). Photographs of the tattoos were taken after 24 hours (Day 1) and 48 hours (Day 2) after the application of the semi-permanent ink on the skin of the user.

To measure the darkness of the tattoo on the skin, the tattoos marks were analyzed using software employing the common RGB color scale method which quantifies colors on a 0-255 scale. A small square image of each of the photos in FIG. 1 was taken for a tattoo treated with a silicone adhesive (right, measurement of the average grayscale value: "Silicon Grayscale Value") and for a tattoo that was not treated with a silicone adhesive (left, measurement of the average grayscale value: "Blank Grayscale Value"). The average grayscale values for the entire image were found (0 is black and 255 is white). The percent decrease in grayscale from tattoos that were not treated with a silicone adhesive to tattoos that were treated with a silicone adhesive was found. This was a negative value as the tattoos treated with the silicone adhesive were darker for everyone which meant the grayscale value was lower on a scale of 0 to 255. The average decrease in grayscale and standard deviation for all samples were found.

Figure 1:
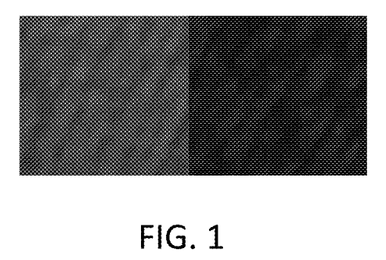
FIG. 1 shows photos taken for a tattoo treated with a silicone adhesive (right) and for a tattoo that was not treated with a silicone adhesive (left).

Day 1:
  Sample: 1
  Blank Grayscale Value: 80.84032258064515
  Silicon Grayscale Value: 38.12267904509285%
  % Decrease in Grayscale (i.e. −ve % Increase in Darkness): −52.84%
Day 2:
  Sample: 1
  Blank Grayscale Value: 108.55927291886198
  Silicon Grayscale Value: 72.00641025641025

As the two conditions were close to each other and on the same image, the general photo-taking conditions were kept constant, which allowed for a comparison of small squares of ink blobs with each other in terms of darkness (grayscale values). The difference between these grayscale values for the silicone vs no silicone was determined and an average obtained.

Semi-permanent tattoos were hand drawn on several subjects. Part of the semi-permanent tattoos were treated with the above mentioned silicone adhesive (see Row S of FIG. 2) as per the above described protocol and part of the semi-permanent tattoos were not treated with the silicone adhesive (see Row B of FIG. 2).

Figure 2:
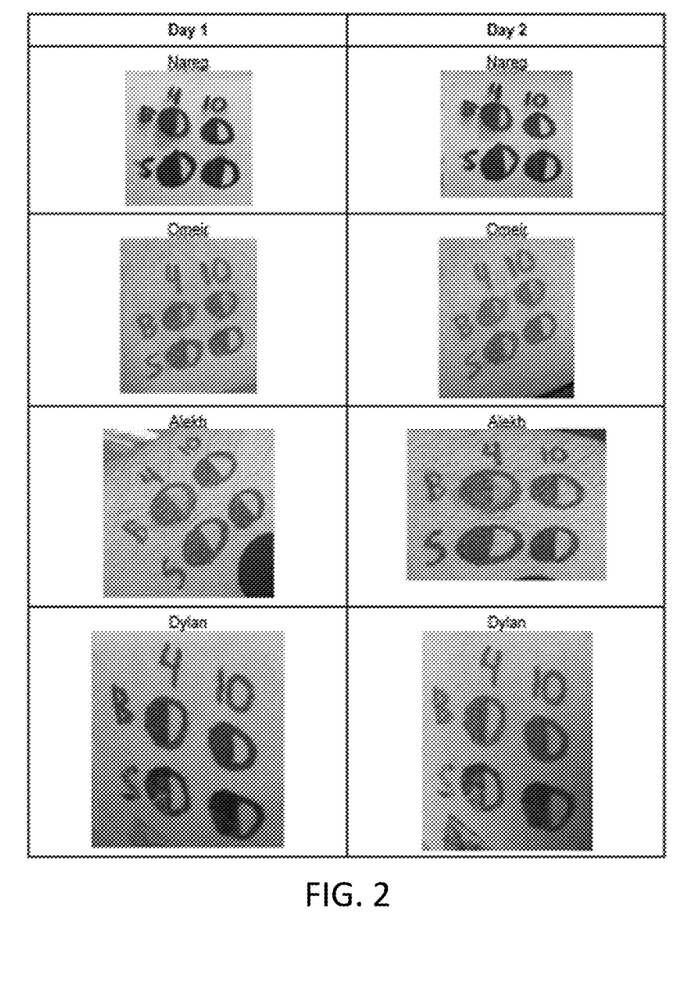
FIG. 2 shows photos comparing hand drawn semi-permanent ink tattoos treated with a silicone adhesive (labeled as Row S) and not treated with a silicone adhesive (labeled as Row B) for several subjects.

FIG. 2 shows how the application of the silicone adhesive improves the performance of tattoos hand drawn using a semi-permanent ink marker. In the table 4 below, the darkness of these tattoos (with and without the silicone adhesive) was evaluated visually by using a 1 to 4 scale, wherein 1 corresponds to the faintest visually detectable blue skin coloration, and 4 corresponds to the maximum darkness (deep blue) achievable by a genipin skin tattoo (i.e. a dark blue color that is close to black). The visual assessment and scoring has been conducted by experts used to conduct such assessment.

TABLE 4

|  | Day 1 (without silicone adhesive) | Day 2 (without silicone adhesive) | Day 1 (with silicone adhesive) | Day 2 (with silicone adhesive) |
| --- | --- | --- | --- | --- |
| Nareg | 4 | 4 | 4 | 4 |
| Omeir | 2 | 2 | 3 | 3 |
| Alekh | 3 | 3 | 3 | 4 |
| Dylan | 4 | 4 | 4 | 4 |
| Diego | 2 | 2 | 3 | 3 |
| Ethan | 4 | 4 | 4 | 4 |
| Ian | 2 | 2 | 3 | 3 |
| Ingrid | 2 | 2 | 2 | 2 |
| James | 2 | 2 | 3 | 3 |
| Leah | 4 | 4 | 4 | 4 |

In conclusion, for a significant number of test subjects, the application of a silicone adhesive patch over the area of tattoo application increases both the final darkness achieved as well as the speed at which the tattoo darkens (i.e. less time is needed to achieve the final darkness of the tattoo). Additionally, by allowing the tattoo to develop faster and/or darker, an increase in the longevity of the tattoos on the skin has been observed.

Finally, other adhesives made from other materials (other than silicone-based adhesives) have been used, which are non-silicone adhesives in particular an adhesive made from synthetic rubber and an acrylic-based adhesive. However, such non-silicone adhesives resulted in "bleeding" of the semi-permanent ink (in other words running of the tattoo colors) and also they adhered to the tattoo (comprising the semi-permanent ink) to the point where they peeled it off. A polyethylene-based wrap (which is also a non-silicone adhesive) has also been used, but resulted as well in some "bleeding" of the semi-permanent inks.

Other Embodiments

Embodiment 1 is a transfer medium comprising:
a solvent present in an amount of about 85% to about 95% w/w of the transfer medium;
a thickening agent present in an amount of about 1% to about 5% w/w of the transfer medium; and
a humectant present in an amount of about 1% to about 5% w/w of the transfer medium.

Embodiment 2 is the transfer medium of embodiment 1, wherein the solvent is present in an amount of about 93% w/w of the transfer medium.

Embodiment 3 is the transfer medium of any one of embodiments 1-2, wherein the solvent comprises water.

Embodiment 4 is the transfer medium of any one of embodiments 1-3, wherein the thickening agent is present in an amount of about 3.5% w/w of the transfer medium.

Embodiment 5 is the transfer medium of embodiment 4, wherein the thickening agent comprises a crosslinked polyacrylate polymer, acrylates copolymer, or combinations thereof.

Embodiment 6 is the transfer medium of embodiment 5, wherein the crosslinked polyacrylate polymer is polyvinyl carboxy polymer crosslinked with ethers of pentaerythritol.

Embodiment 7 is the transfer medium of any one of embodiments 1-6, wherein the humectant is present in an amount of about 2% w/w of the transfer medium.

Embodiment 8 is the transfer medium of any one of embodiments 1-7, wherein the humectant comprises propanediol.

Embodiment 9 is the transfer medium of any one of embodiments 1-8, wherein the transfer medium further comprises a preservative.

Embodiment 10 is the transfer medium of any one of embodiments 1-9 wherein the preservative is present in an amount of about 0.5% to about 1.5% w/w of the transfer medium.

Embodiment 11 is the transfer medium of any one of embodiments 1-10, wherein the preservative is present in an amount of about 1% w/w of the transfer medium.

Embodiment 12 is the transfer medium of any one of embodiments 1-11, wherein the preservative comprises EDTA and/or sodium phytate.

Embodiment 13 is the transfer medium of embodiment 12, wherein the EDTA and/or sodium phytate is present in an amount of about 0.01% to about 1% w/w of the transfer medium.

Embodiment 14 is the transfer medium of any one of embodiments 12-13, wherein the EDTA and/or sodium phytate is present in an amount of about 0.1% w/w of the transfer medium.

Embodiment 15 is the transfer medium of any one of embodiments 11-14, wherein the preservative comprises a combination of phenoxyethanol and ethylhexylglycerin.

Embodiment 16 is the transfer medium of embodiment 15, wherein the combination of phenoxyethanol and ethylhexylglycerin is present in the composition at a ratio of about 9:1 phenoxyethanol:ethylhexylglycerin.

Embodiment 17 is the transfer medium of embodiment 15 or 16, wherein the combination of phenoxyethanol and ethylhexylglycerin is present in an amount of about 0.1% to about 2% w/w of the transfer medium.

Embodiment 18 is the transfer medium of any one of embodiments 14-17 wherein the combination of phenoxyethanol and ethylhexylglycerin is present in an amount of about 1% w/w of the transfer medium.

Embodiment 19 is the transfer medium of any one of embodiments 1-18, wherein the transfer medium further comprises a pH adjuster.

Embodiment 20 is the transfer medium of embodiment 19, wherein the pH adjuster is present in an amount of about 0.1% to about 1% w/w of the transfer medium.

Embodiment 21 is the transfer medium embodiment 19 or 20, wherein the pH adjuster comprises triethanolamine and/or sodium hydroxide.

Embodiment 22 is a method for applying ink to skin, the method comprising:
- (a) disposing a transfer medium on a portion of skin;
- (b) applying an applicator comprising ink disposed thereon to the portion of skin to thereby transfer the ink to the portion of skin; and
- (c) removing the applicator from the portion of skin.

Embodiment 23 is the method of embodiment 22, wherein the method further comprises: (d) depositing semi-permanent ink on the portion of the skin.

Embodiment 24 is the method of embodiment 22 or 23, wherein the ink is a medical-grade ink.

Embodiment 25 is the method of any one of embodiments 22-24, wherein the ink is removable from skin using an alcohol.

Embodiment 26 is the method of embodiment 25, wherein the alcohol comprises ethanol, isopropyl alcohol, or a combination thereof.

Embodiment 27 is the method of any one of embodiments 22-26, wherein the ink is disposed on the applicator as a design, and wherein the design is a pattern, a shape, a symbol, one or more words, a picture, an image created by a user, or combinations thereof.

Embodiment 28 is the method of any one of embodiments 22-27, wherein the semi-permanent ink comprises genipin, a genipin derivative, lawsone, a lawsone derivative, or combinations thereof.

Embodiment 29 is the method of embodiment 28, wherein the semi-permanent ink further comprises one or more of: a solvent; a humectant; a thickening agent; semi-volatile semi-permanent colorant solubilizer; and a film-forming agent.

Embodiment 30 is the method of embodiment 28, wherein the semi-permanent ink further comprises one or more of: a solvent; a humectant; and a film-forming agent.

Embodiment 31 is the method of any one of embodiments 22-30, wherein the semi-permanent tattoo is applied to the skin on a user's forearm, leg, shoulder, bicep, torso, face, neck, or back.

Embodiment 32 is the method of any one of embodiments 22-31, wherein the method further comprises: (e) applying a silicone adhesive and/or a silicone spray composition to the skin over the semi-permanent tattoo.

Embodiment 33 is the method of any one of embodiments 22-32, wherein the transfer medium is the transfer medium of any one of embodiments 1-22.

Embodiment 34 is a method for increasing the longevity of a semi-permanent ink in skin, the method comprising applying a silicone medium to the skin.

Embodiment 35 is the method of embodiment 34, wherein the silicone medium comprises:
- dimethylpolysiloxane present in an amount of about 75% to about 85% w/w of the silicone medium; and
- hydroxy-terminated dimethyl siloxane present in an amount of about 5% to about 15% w/w of the silicone medium.

Embodiment 36 is the method of embodiment 34 or 35, wherein the silicone medium comprises:
- dimethylpolysiloxane present in an amount of about 75% to about 85% w/w of the silicone medium;
- hydroxy-terminated dimethyl siloxane present in an amount of about 5% to about 15% w/w of the silicone medium;
- dodecamethyl cyclohexasiloxane present in an amount of less than about 0.001% to about 1% of w/w of the silicone medium; and
- decamethylcyclopentasiloxane present in an amount of less than about 0.001% to about 1% of w/w of the silicone medium.

Embodiment 37 is the method of any one of embodiments 34-36, wherein the silicone medium does not comprise one or more of water, ethanol, and isopropanol.

Embodiment 38 is the method of any one of embodiments 34-37, wherein the silicone medium is applied to the skin over the semi-permanent tattoo.

Embodiment 39 is the method of any one of embodiments 34-38, wherein the silicone medium is applied to the skin over a portion of the semi-permanent tattoo.

Embodiment 40 is the method of any one of embodiments 34-38, wherein the silicone medium is applied to the skin over the entire semi-permanent tattoo.

Embodiment 41 is the method of any one of embodiments 34-40, wherein the silicone medium is applied to the skin daily.

Embodiment 42 is the method of any one of embodiments 34-40, wherein the silicone medium is applied to the skin twice a day.

Embodiment 43 is the method of any one of embodiments 34-40, wherein the silicone medium is applied to the skin every other day.

Embodiment 44 is the method of any one of embodiments 34-43, wherein the method further comprises applying a silicone adhesive to the skin.

Embodiment 45 is the method of embodiment 44, wherein the silicone adhesive is applied to the skin within about 1 to about 2 hours after the application of the semi-permanent tattoo to the skin.

Embodiment 46 is the method of any one of embodiments 34-45 wherein the silicone medium increases the longevity of the semi-permanent tattoo in the skin by about 1 to about 5 days.

Embodiment 47 is the method of any one of embodiments 34-46, wherein the silicone medium increases the longevity of the semi-permanent tattoo in the skin by about 4 to about 5 days.

Embodiment 48 is a method for increasing the darkness and/or the longevity of a semi-permanent ink in skin and/or for decreasing the time needed for achieving the final darkness of a semi-permanent ink in skin (i.e. for increasing the speed at which the tattoo darkens), the method comprising applying a silicone adhesive to the skin.

Embodiment 49 is the method of embodiment 48, wherein the silicone adhesive is applied to the skin over the semi-permanent tattoo.

Embodiment 50 is the method of embodiment 48 or 49, wherein the silicone adhesive is applied to the skin over a portion of the semi-permanent tattoo.

Embodiment 51 is the method of any one of embodiments 48-50, wherein the silicone adhesive is applied to the skin over the entire semi-permanent tattoo.

Embodiment 52 is the method of embodiment 51, wherein the silicone adhesive is applied to the skin within about 1 to about 2 hours after the application of the semi-permanent tattoo to the skin.

Embodiment 53 is the method of embodiment 52, wherein the silicone adhesive is applied to the skin within about 1 hour after the application of the semi-permanent tattoo to the skin.

Embodiment 54 is the method of embodiment 53, wherein the silicone adhesive is applied to the skin about 10 minutes after the application of the semi-permanent tattoo to the skin.

Embodiment 55 is the method of embodiment 53, wherein the silicone adhesive is applied to the skin about 5 minutes after the application of the semi-permanent tattoo to the skin.

Embodiment 56 is the method of any one of embodiments 48-55, wherein the silicone adhesive is removed from the skin about 1 to about 10 hours after the application of the silicone adhesive to the skin.

Embodiment 57 is the method of any one of embodiments 48-56, wherein the silicone adhesive is removed from the skin about 5 to about 10 hours after the application of the silicone adhesive to the skin.

Embodiment 58 is the method of any one of embodiments 48-57, wherein the silicone adhesive is removed from the skin about 6 to about 8 hours after the application of the silicone adhesive to the skin.

Embodiment 59 is the method of any one of embodiments 48-56, wherein the silicone adhesive is removed from the skin about 1 to about 2 hours after the application of the silicone adhesive to the skin.

Embodiment 60 is the method of any one of embodiments 48-59, wherein the method further comprises applying a silicone medium to the skin.

Embodiment 61 is the method of any one of embodiments 48-60, wherein the silicone medium is applied to the skin daily.

Embodiment 62 is the method of any one of embodiments 48-60, wherein the silicone medium is applied to the skin twice a day.

Embodiment 63 is the method of any one of embodiments 48-60 wherein the silicone medium is applied to the skin every other day.

Embodiment 64 is the method of any one of embodiments 48-63, wherein the silicone medium comprises:
  dimethylpolysiloxane present in an amount of about 75% to about 85% w/w of the silicone medium; and
  hydroxy-terminated dimethyl siloxane present in an amount of about 5% to about 15% w/w of the silicone medium.

Embodiment 65 is the method of embodiment 64, wherein the silicone medium comprises:
  dimethylpolysiloxane present in an amount of about 75% to about 85% w/w of the silicone medium;
  hydroxy-terminated dimethyl siloxane present in an amount of about 5% to about 15% w/w of the silicone medium;
  dodecamethyl cyclohexasiloxane present in an amount of less than about 0.001% to about 1% of w/w of the silicone medium; and
  decamethylcyclopentasiloxane present in an amount of less than about 0.001% to about 1% of w/w of the silicone medium.

Embodiment 66 is the method of any one of embodiments 48-65, wherein the silicone medium does not comprise one or more of water, ethanol, and isopropanol.

Embodiment 67 is a kit comprising:
a semi-permanent ink;
a silicone adhesive and/or a silicone medium.

Embodiment 68 is a kit comprising:
a transfer medium; and
a silicone adhesive and/or a silicone medium.

Embodiment 69 is a kit comprising:
a transfer medium; and
a silicone adhesive and/or a semi-permanent ink.

Embodiment 70 is a kit comprising:
a semi-permanent ink;
a transfer medium; and
a silicone adhesive and/or a silicone medium.

Embodiment 71 is the kit of embodiment 68, wherein the kit further comprises a semi-permanent ink.

Embodiment 72 is the kit of any one of embodiments 67-71, wherein the kit further comprises an ink applicator.

Embodiment 73 is the kit of embodiment 72, wherein the ink applicator is a marker.

Embodiment 74 is the kit of any one of embodiments 67 and 70-73, wherein the semi-permanent ink comprises genipin, a genipin derivative, lawsone, a lawsone derivative, or combinations thereof.

Embodiment 75 is the kit of embodiment 74, wherein the semi-permanent ink further comprises one or more of: a solvent; a humectant; a thickening agent; semi-volatile semi-permanent colorant solubilizer; and a film-forming agent.

Embodiment 76 is the kit of embodiment 75, wherein the semi-permanent ink further comprises one or more of: a solvent; a humectant; and a film-forming agent.

Embodiment 77 is the kit of any one of embodiments 67-76, wherein the transfer medium is the transfer medium of any one of embodiments 1-21.

Embodiment 78 is the kit of any one of embodiments 67-77, wherein silicone adhesive comprises a silicone gel adhesive disposed on a polycarbonate backing, more specifically wherein the silicone adhesive comprises a silicone gel adhesive coated onto a polyurethane carrier and is disposed on a polycarbonate backing.

Embodiment 79 is the kit of any one of embodiments 67-78, wherein the silicone gel adhesive has an adhesive coat weight of at least about 100 gsm.

Embodiment 80 is the kit of any one of embodiments 67-79, wherein the silicone gel adhesive has an adhesive coat weight of about 100 gsm to about 300 gsm.

Embodiment 81 is the kit of any one of embodiments 67-78, wherein the silicone gel adhesive has an adhesive coat weight of about 150 gsm.

Embodiment 82 is the kit of any one of embodiments 67-81, wherein the silicone medium comprises:
  dimethylpolysiloxane present in an amount of about 75% to about 85% w/w of the silicone medium; and
  hydroxy-terminated dimethyl siloxane present in an amount of about 5% to about 15% w/w of the silicone medium.

Embodiment 83 is the kit of embodiment 82, wherein the silicone medium comprises:
  dimethylpolysiloxane present in an amount of about 75% to about 85% w/w of the silicone medium;
  hydroxy-terminated dimethyl siloxane present in an amount of about 5% to about 15% w/w of the silicone medium;
  dodecamethyl cyclohexasiloxane present in an amount of less than about 0.001% to about 1% of w/w of the silicone medium; and
  decamethylcyclopentasiloxane present in an amount of less than about 0.001% to about 1% of w/w of the silicone medium.

Embodiment 84 is the kit of any one of embodiments 67-83, wherein the silicone medium does not comprise one or more of water, ethanol, and isopropanol.

Embodiment 85 is the kit of any one of embodiments 67-84, wherein the kit further comprises an applicator.

Embodiment 86 is the kit of embodiment 85, wherein the applicator is pre-cut.

Embodiment 87 is the kit of embodiment 89, wherein the applicator is pre-cut into a rectangular shape.

Embodiment 88 is the kit of any one of embodiments 85-87, wherein the applicator comprises paper.

Embodiment 89 is the kit of any one of embodiments 67-88, wherein the kit further comprises ink.

Embodiment 90 is the kit of embodiment 89, wherein the ink comprises medical-grade ink.

Embodiment 91 is the kit of embodiments 89 or 90, wherein the ink is removable from skin using an alcohol.

Embodiment 92 is the kit of any one of embodiments 67-91, wherein the kit further comprises a glove.

Embodiment 93 is the kit of any one of embodiments 67-92, wherein the kit further comprises instructions describing a method of any one of embodiments 22-66.

Embodiment 94 is a silicone medium comprising:
dimethylpolysiloxane present in an amount of about 75% to about 85% w/w of the silicone medium; and
hydroxy-terminated dimethyl siloxane present in an amount of about 5% to about 15% w/w of the silicone medium.

Embodiment 95 is the silicone medium of embodiment 94, wherein the silicone medium comprises:
dimethylpolysiloxane present in an amount of about 75% to about 85% w/w of the silicone medium;
hydroxy-terminated dimethyl siloxane present in an amount of about 5% to about 15% w/w of the silicone medium;
dodecamethyl cyclohexasiloxane present in an amount of less than about 0.001% to about 1% of w/w of the silicone medium; and
decamethylcyclopentasiloxane present in an amount of less than about 0.001% to about 1% of w/w of the silicone medium.

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A method for applying ink to skin, the method comprising:
   (a) disposing a transfer medium on a portion of skin, wherein the transfer medium includes:
      a solvent present in an amount of about 85% to about 95% w/w of the transfer medium;
      a thickening agent present in an amount of about 1% to about 5% w/w of the transfer medium; and
      a humectant present in an amount of about 1% to about 5% w/w of the transfer medium;
   (b) applying an applicator comprising an ink disposed thereon to the portion of skin to thereby transfer the ink to the portion of skin;
   (c) removing the applicator from the portion of skin; and
   (d) applying a silicone adhesive over the ink on the portion of skin.

2. The method of claim 1, wherein the method further comprises: (e) depositing a semi-permanent ink on the portion of the skin.

3. The method of claim 1, wherein the ink is a medical-grade ink.

4. The method of claim 1, wherein the ink is removable from skin using an alcohol.

5. The method of claim 2, wherein the semi-permanent ink comprises genipin, a genipin derivative, lawsone, a lawsone derivative, or combinations thereof.

6. The method of claim 5, wherein the semi-permanent ink further comprises one or more of: a solvent; a humectant; a thickening agent; semi-volatile semi-permanent colorant solubilizer; and a film-forming agent.

7. A method for increasing a darkness and/or longevity of a semi-permanent ink in skin, the method comprising:
disposing a transfer medium on a portion of skin;
applying the semi-permanent ink to the portion of skin to form a semi-permanent tattoo; and
applying a silicone adhesive to the portion of skin over the semi-permanent tattoo.

8. The method of claim 7, wherein the silicone adhesive is applied to the skin within about 1 to about 2 hours after the application of the semi-permanent ink to the portion of skin, or wherein the silicone adhesive is applied to the skin about 10 minutes after the application of the semi-permanent ink to the portion of skin, or about 5 minutes after the application of the semi-permanent ink to the portion of skin.

9. The method of claim 7, wherein the silicone adhesive is removed from the skin about 1 to about 10 hours after the application of the silicone adhesive to the skin, or about 5 to about 10 hours after the application of the silicone adhesive to the skin, or about 6 to about 8 hours after the application of the silicone adhesive to the portion of skin, or about 1 to about 2 hours after the application of the silicone adhesive to the portion of skin.

10. A kit for applying tattoos comprising:
a semi-permanent ink;
a silicone adhesive; and
a transfer medium, wherein the transfer medium includes:
   a solvent present in an amount of about 85% to about 95% w/w of the transfer medium;
   a thickening agent present in an amount of about 1% to about 5% w/w of the transfer medium; and
   a humectant present in an amount of about 1% to about 5% w/w of the transfer medium.

11. The kit of claim 10, wherein the semi-permanent ink comprises genipin, a genipin derivative, lawsone, a lawsone derivative, or combinations thereof.

12. The kit of claim 10, wherein the semi-permanent ink further comprises one or more of: a solvent; a humectant; a thickening agent; semi-volatile semi-permanent colorant solubilizer; and a film-forming agent.

13. The kit of claim 10, wherein the kit further comprises an applicator.

* * * * *